United States Patent
Macevicz

(10) Patent No.: US 6,306,597 B1
(45) Date of Patent: *Oct. 23, 2001

(54) DNA SEQUENCING BY PARALLEL OLIGONUCLEOTIDE EXTENSIONS

(75) Inventor: Stephen C. Macevicz, Cupertino, CA (US)

(73) Assignee: Lynx Therapeutics, Inc., Hayward, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/280,270

(22) Filed: Mar. 29, 1999

Related U.S. Application Data

(60) Continuation of application No. 08/872,446, filed on Jun. 10, 1997, now Pat. No. 5,969,119, which is a division of application No. 08/424,663, filed on Apr. 17, 1995, now Pat. No. 5,750,341.

(51) Int. Cl.[7] .............................. C12Q 1/68; C12P 19/34; G01N 33/00; C07H 21/02; C07H 21/04
(52) U.S. Cl. ..................... 435/6; 435/91.1; 435/91.2; 436/94; 536/23.1; 536/24.3; 536/24.33
(58) Field of Search .............................. 435/6, 91.1, 91.2, 435/183; 536/23.1, 24.3, 24.33, 25.3; 436/94

(56) References Cited

U.S. PATENT DOCUMENTS

| | | |
|---|---|---|
| 5,002,867 | 3/1991 | Macevicz ................................. 435/6 |
| 5,013,830 | 5/1991 | Ohtsuka et al. ...................... 536/27 |
| 5,114,839 | 5/1992 | Blocker .................................... 435/6 |
| 5,367,066 | 11/1994 | Urdea et al. ........................ 536/24.3 |
| 5,403,708 | 4/1995 | Brennan et al. ........................ 435/6 |
| 5,407,799 | 4/1995 | Studier ..................................... 435/6 |
| 5,503,890 | 4/1996 | Cantor ..................................... 435/6 |
| 5,679,524 | * 10/1997 | Nikiforov et al. ...................... 435/6 |
| 5,750,341 | * 5/1998 | Macevicz ................................. 435/6 |

FOREIGN PATENT DOCUMENTS

| | | |
|---|---|---|
| 0 549 107 A1 | 6/1993 | (EP). |
| WO 91/12323 | 8/1991 | (WO). |
| WO 95/20053 | 7/1995 | (WO). |

OTHER PUBLICATIONS

Pease et al., Light–generated oligonucleotide arrays for rapid DNA sequence analysis. Proc. Natl. Acad. Sci. USA 91, 3022–5026, May 1994.*

Stratagene catalog (1994), p. 109. Published by Stratagene Cloning Systems, 11011 North Torrey Pines Road, La Jolla, Ca 92037.*

Chretien et al., "Multiplex Random Priming of Internal Restriction Fragments for DNA Sequencing," *DNA and Cell Biology*. 11:337–343 (1992).

Hou et al., "Fluorescence–Based DNA Sequencing with Hexamer Primers," *Nucleic Acids Research*. 21: 3331–3332 (1993).

Kaczorowski et al., "Assembly of 18–Nucleotide Primers by Ligation of Three Hexamers: Sequencing of Large Genomes by Primer Walking," *Anal. Biochem*. 221:127–135 (1994).

Kieleczawa et al., "DNA Sequencing by Primer Walking with Strings of Contiguous Hexamers," *Science*, 258: 1787–1790 (1992).

Kotler et al., "DNA Sequencing: Modular Primers Assembled from a Library of Hexamers or Pentamers," *Proc. Natl. Acad. Sci*. 90: 4241–4245 (1993).

(List continued on next page.)

Primary Examiner—Ethan Whisenant
Assistant Examiner—Frank Lu
(74) Attorney, Agent, or Firm—Stephen C. Macevicz; Vincent M. Powers; LeeAnn Gorthey

(57) ABSTRACT

The present invention includes, in one aspect, a kit comprising one or more sets of oligonucleotide probes whose perfectly matched duplexes with complementary sequences have similar or substantially the same free energy of duplex formation.

8 Claims, 5 Drawing Sheets

OTHER PUBLICATIONS

Studier, "A Strategy for High–Volume Sequencing of Cosmid DNAs: Random and Directed Priming with a Library of Oligonucleotides," *Proc. Natl. Acad Sci.* 86: 6917–6921 (1989).

Szybalski, "Proposal for Sequencing DNA Using Ligation of Hexamers to Generate Sequential Elongation Primers (SPEL–6)," *Gene*. 90: 177–178 (1990).

* cited by examiner

```
                         SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
         (A) LENGTH: 37 base pairs
         (B) TYPE: nucleic acid
         (C) STRANDEDNESS: single
         (D) TOPOLOGY: linear (xi) SEQUENCE DESCRIPTION: SEQ ID NO: 1:

CCTCTCCCTT CCCTCTCCTC CCTCTCCCCT CTCCCTC                             37

(2) INFORMATION FOR SEQ ID NO: 2:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (xi) SEQUENCE DESCRIPTION: SEQ ID NO: 2:

GAGGAGAGGG AAGGAGAGGA G                                              21

(2) INFORMATION FOR SEQ ID NO: 3:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (xi) SEQUENCE DESCRIPTION: SEQ ID NO: 3:

GGAGGAGAGG GAAGGAGAGG A                                              21

(2) INFORMATION FOR SEQ ID NO: 4:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (xi) SEQUENCE DESCRIPTION: SEQ ID NO: 4:

GGGAGGAGAG GGAAGGAGAG G                                              21

(2) INFORMATION FOR SEQ ID NO: 5:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (xi) SEQUENCE DESCRIPTION: SEQ ID NO: 5:

AGGGAGGAGA GGGAAGGAGA G                                              21
```

(2) INFORMATION FOR SEQ ID NO: 6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 6:

GAGGGAGAGG GGAGAGGG                                            18

(2) INFORMATION FOR SEQ ID NO: 7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 7:

ACCGTCTCCG GGAGCTGC                                            18

(2) INFORMATION FOR SEQ ID NO: 8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 8:

CCTCTCCCTT CCCTCTCCTC C                                      21

(2) INFORMATION FOR SEQ ID NO: 9:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO: 9:

CCGGGAGGGA GAGGGGAGAG GGAGGAGAGG GAAGGGAGAG GAGCT            45

(2) INFORMATION FOR SEQ ID NO: 10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 10:

CCCTCTCCCC TCTCCCTC                                            18

(2) INFORMATION FOR SEQ ID NO: 11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 11:

GCAGCTCCCG GAGACGGT                                            18

(2) INFORMATION FOR SEQ ID NO: 12:

```
        (i) SEQUENCE CHARACTERISTICS:
            (A) LENGTH: 48 base pairs
            (B) TYPE: nucleic acid
            (C) STRANDEDNESS: single
            (D) TOPOLOGY: linear (xi) SEQUENCE DESCRIPTION: SEQ ID NO: 12:

TGAATTCGAG CTCCTCTCCT TCCCTCTCCT CCCTCTCCCC TCTCCCTC                    48

(2) INFORMATION FOR SEQ ID NO: 13:

(i) SEQUENCE CHARACTERISTICS:
            (A) LENGTH: 7 base pairs
            (B) TYPE: nucleic acid
            (C) STRANDEDNESS: single
            (D) TOPOLOGY: linear (xi) SEQUENCE DESCRIPTION: SEQ ID NO: 13:

GCAGCTC                                                                  7
```

DNA SEQUENCING BY PARALLEL OLIGONUCLEOTIDE EXTENSIONS

This application is a continuation of Ser. No. 08/872,446, filed Jun. 10, 1997 now U.S. Pat. No. 5,969,119, which is a divisional of Ser. No. 08/424,663, filed Apr. 17, 1995 now U.S. Pat. No. 5,750,341, herein incorporated by reference.

FIELD OF THE INVENTION

The invention relates generally to methods for determining the nucleotide sequence of a polynucleotide, and more particularly, to a method of identifying nucleotides in a template by stepwise extension of one or more primers by successive ligations of oligonucleotide blocks.

BACKGROUND

Analysis of polynucleotides with currently available techniques provides a spectrum of information ranging from the confirmation that a test polynucleotide is the same or different than a standard or an isolated fragment to the express identification and ordering of each nucleoside of the test polynucleotide. Not only are such techniques crucial for understanding the function and control of genes and for applying many of the basic techniques of molecular biology, but they have also become increasingly important as tools in genomic analysis and a great many non-research applications, such as genetic identification, forensic analysis, genetic counselling, medical diagnostics, and the like. In these latter applications both techniques providing partial sequence information, such as fingerprinting and sequence comparisons, and techniques providing full sequence determination have been employed, e.g. Gibbs et al, Proc. Natl. Acad. Sci. 86: 1919–1923 (1989); Gyllenstein et al, Proc. Natl. Acad. Sci, 85:7652–7656 (1988); Carrano et al, Genomics, 4:129–136 (1989); Caetano-Anolles et al, Mol. Gen. Genet, 235:157–165 (1992); Brenner and Livak, Proc. Natl. Acad. Sci., 86:8902–8906 (1989); Green et al, PCR Methods and Applications, 1: 77–90 (1991); and Versalovic et al, Nucleic Acids Research, 19: 6823–6831 (1991).

Native DNA consists of two linear polymers, or strands of nucleotides. Each strand is a chain of nucleosides linked by phosphodiester bonds. The two strands are held together in an antiparallel orientation by hydrogen bonds between complementary bases of the nucleotides of the two strands: deoxyadenosine (A) pairs with thymidine (ID and deoxyguanosine (G) pairs with deoxycytidine (C).

Presently there are two basic approaches to DNA sequence determination: the dideoxy chain termination method, e.g. Sanger et al, Proc. Natl. Acad. Sci. 74 :5463–5467 (1977); and the chemical degradation method, e.g. Maxam et al, Proc. Natl. Acad. Sci. 74: 560–564 (1977). The chain termination method has been improved in several ways, and serves as the basis for all currency available automated DNA sequencing machines, e.g. Sanger et al, J. Mol. Biol., 143: 161–178 (1980); Schreier et al, J. Mol. Biol., 129: 169–172 (1979); Smith et al, Nucleic Acids Research, 13: 2399–2412 (1985); Smith et al, Nature, 321: 674–679 (1987); Prober et al, Science, 238: 336–341 (1987); Section II, Meth. Enzmol., 155: 51–334 (1987); Church et al, Science, 240: 185–188 (1988); Hunkapiller et al, Science, 254: 59–67 (1991); Bevan et al, PCR Methods and Applications, 1: 222–228 (1992).

Both the chain termination and chemical degradation methods require the generation of one or more sets of labeled DNA fragments, each having a common origin and each terminating with a known base. The set or sets of fragments must then be separated by size to obtain sequence information. In both methods, the DNA fragments are separated by high resolution gel electrophoresis, which must have the capacity of distinguishing very large fragments differing in size by no more than a single nucleotide. Unfortunately, this step severely limits the size of the DNA chain that can be sequenced at one time. Sequencing using these techniques can reliably accommodate a DNA chain of up to about 400–450 nucleotides, Bankier et al, Meth. Enzymol., 155: 51–93 (1987); and Hawkins et al, Electrophoresis, 13: 552–559 (1992).

Several significant technical problems have seriously impeded the application of such techniques to the sequencing of long target polynucleotides, e.g. in excess of 500–600 nucleotides, or to the sequencing of high volumes of many target polynucleotides. Such problems include i) the gel electrophoretic separation step which is labor intensive, is difficult to automate, and introduces an extra degree of variability in the analysis of data, e.g. band broadening due to temperature effects, compressions due to secondary structure in the DNA sequencing fragments, inhomogeneities in the separation gel, and the like; ii) nucleic acid polymerases whose properties, such as processivity, fidelity, rate of polymerization, rate of incorporation of chain terminators, and the like, are often sequence dependent; iii) detection and analysis of DNA sequencing fragments which are typically present in fmol quantities in spacially overlapping bands in a gel; iv) lower signals because the labelling moiety is distributed over the many hundred spacially separated bands rather than being concentrated in a single homogeneous phase, and v) in the case of single-lane fluorescence detection, the availability of dyes with suitable emission and absorption properties, quantum yield, and spectral resolvability, e.g. Trainor, Anal. Biochem., 62: 418–426 (1990); Connell et al, Biotechniques, 5: 342–348 (1987); Karger et al, Nucleic Acids Research, 19: 4955–4962 (1991); Fung et al, U.S. Pat. No. 4,855,225; and Nishikawa et al, Electrophoresis, 12: 623–631 (1991).

Another problem exists with current technology in the area of diagnostic sequencing. An ever widening array of disorders, susceptibilities to disorders, prognoses of disease conditions, and the like, have been correlated with the presence of particular DNA sequences, or the degree of variation (or mutation) in DNA sequences, at one or more genetic loci. Examples of such phenomena include human leukocyte antigen (HLA) typing, cystic fibrosis, tumor progression and heterogeneity, p53 proto-oncogene mutations, ras proto-oncogene mutations, and the like, e.g. Gyllensten et al, PCR Methods and Applications, 1: 91–98 (1991); Santamaria et al, International application PCT/US92/01675; Tsui et al, International application PCT/CA90/00267; and the like. A difficulty in determining DNA sequences associated with such conditions to obtain diagnostic or prognostic information is the frequent presence of multiple subpopulations of DNA, e.g. allelic variants, multiple mutant forms, and the like. Distinguishing the presence and identity of multiple sequences with current sequencing technology is virtually impossible, without additional work to isolate and perhaps clone the separate species of DNA.

A major advance in sequencing technology could be made if an alternative approach was available for sequencing DNA that did not require high resolution electrophoretic separations of DNA fragments, that generated signals more amenable to analysis, and that provided a means for readily analyzing DNA from heterozygous genetic loci.

An objective of the invention is to provide such an alternative approach to presently available DNA sequencing technologies.

SUMMARY OF THE INVENTION

The invention provides a method of nucleic acid sequence analysis based on repeated cycles of duplex extension along a single stranded template. Preferably, such extension starts from a duplex formed between an initializing oligonucleotide and the template. The initializing oligonucleotide is extended in an initial extension cycle by ligating an oligonucleotide probe to its end to form an extended duplex. The extended duplex is then repeatedly extended by subsequent cycles of ligation. During each cycle, the identity of one or more nucleotides in the template is determined by a label on, or associated with, a successfully ligated oligonucleotide probe. Preferably, the oligonucleotide probe has a blocking moiety, e.g. a chain-terminating nucleotide, in a terminal position so that only a single extension of the extended duplex takes place in a single cycle. The duplex is further extended in subsequent cycles by removing the blocking moiety and regenerating an extendable terminus.

In one aspect of the invention, a plurality of different initializing oligonucleotides is provided for separate samples of the template. Each initializing oligonucleotide forms a duplex with the template such that the end undergoing extension is one or more nucleotides out of register, or phase, with that of every other initializing oligonucleotide of the plurality. In other words, the starting nucleotide for extension is different by one or more nucleotides for each of the different initializing oligonucleotides. In this manner, after each cycle of extension with oligonucleotide probes of the same length, the same relative phase exists between the ends of the initializing oligonucleotides on the different templates. Thus, in a preferred embodiment, where, for example, i) the initializing oligonucleotides are out of phase by one nucleotide, ii) 9-mer oligonucleotide probes are used in the extension step, and iii) nine different initializing oligonucleotides are employed, nine template nucleotides will be identified simultaneously in each extension cycle.

DEFINITIONS

As used herein "sequence determination," "determining a nucleotide sequence," "sequencing," and like terms, in reference to polynucleotides includes determination of partial as well as full sequence information of the polynucleotide. That is, the term includes sequence comparisons, fingerprinting, and like levels of information about a target polynucleotide, as well as the express identification and ordering of each nucleoside of the test polynucleotide.

"Perfectly matched duplex" in reference to the protruding strands of probes and target polynucleotides means that the protruding strand from one forms a double stranded structure with the other such that each nucleotide in the double stranded structure undergoes Watson-Crick basepairing with a nucleotide on the opposite strand The term also comprehends the pairing of nucleoside analogs, such as deoxyinosine, nucleosides with 2-aminopurine bases, and the like, that may be employed to reduce the degeneracy of probes.

The term "oligonucleotide" as used herein includes linear oligomers of nucleosides or analogs thereof, including deoxyribonucleosides, ribonucleosides, and the like, Usually oligonucleotides range in size from a few monomeric units, e.g. 3–4, to several hundreds of monomeric units. Whenever an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted.

As used herein, "nucleoside" includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described generally by Scheit, Nucleotide Analogs (John Wiley, New York, 1980). Such analogs include synthetic nucleosides designed to enhance binding properties, reduce degeneracy, increase specificity, and the like.

As used herein, "ligation" means to form a covalent bond or linkage between the termini of two or more nucleic acids, e.g. oligonucleotides and/or polynucleotides, in a template-driven reaction. The nature of the bond or linkage may vary widely and the ligation may be carried out enzymatically or chemically.

DETAILED DESCRIPTION OF THE INVENTION

The invention provides a method of sequencing nucleic acids which obviates electrophoretic separation of similarly sized DNA fragments, and which eliminates the difficulties associated with the detection and analysis of spacially overlapping bands of DNA fragments in a gel or like medium. The invention also obviates the need to generate DNA fragments from long single stranded templates with a DNA polymerase.

Figure 1:
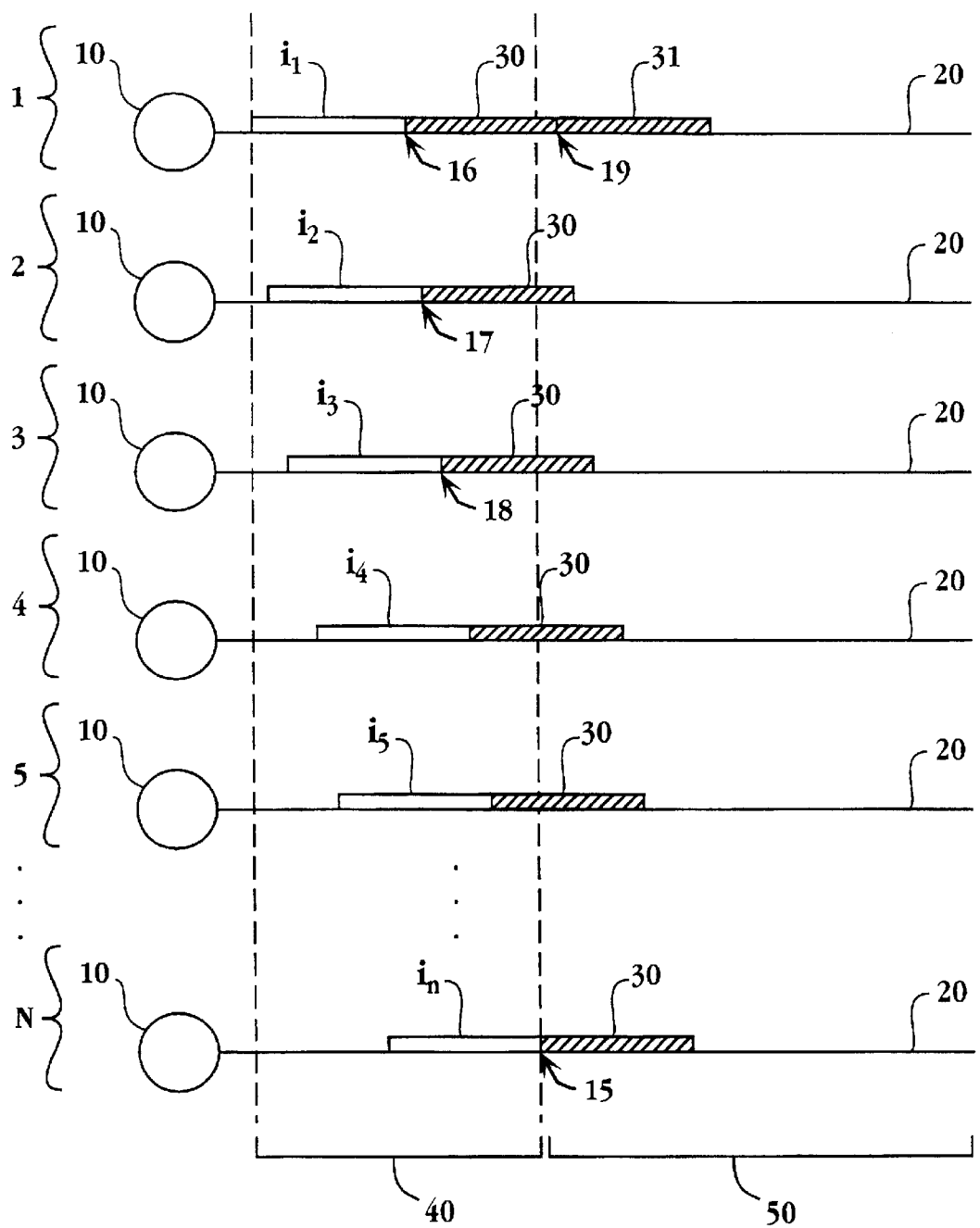
FIG. 1 diagrammatically illustrates parallel extensions of multiple templates in accordance with the invention.

The general scheme of one aspect of the invention is shown diagrammatically in FIG. 1. As described more fully below, the invention is not meant to be limited by the particular features of this embodiment. Template (20) comprising a polynucleotide (50) of unknown sequence and binding region (40) is attached to solid phase support (10). Preferably, for embodiments employing N-mer probes, the template is divided into N aliquots, and for each aliquot a different initializing oligonucleotide $i_k$ is provided that forms a perfectly matched duplex at a location in binding region (40) different from that of the other initializing oligonucleotides. That is, the initializing oligonucleotides $i_1$–$i_N$ form a set of duplexes with the template in the binding region (40), such that the ends of the duplexes proximal to the unknown sequence are from 0 to N−1 nucleotides from the start of the unknown sequence. Thus, in the first cycle of ligations with N-mer probes, a terminal nucleotide (16) of probe (30) ligated to $i_1$ in FIG. 1 will be complementary to the N−1 nucleotide of binding region (40). Likewise, a terminal nucleotide (17) of probe (30) ligated to $i_2$ in FIG. 1 will be complementary to the N−2 nucleotide of binding region (40); a terminal nucleotide (18) of probe (30) ligated to $i_3$ in FIG. 1 will be complementary to the N−3 nucleotide of binding region (40), and so on. Finally, a terminal nucleotide (15) of probe (30) ligated to in will be complementary to the first nucleotide of unknown sequence (50). In the second cycle of ligations, a terminal nucleotide (19) of probe (31) will be complementary to the second nucleotide (19) of unknown sequence (50) in duplexes starting with initializing oligonucleotide $i_1$. Likewise, terminal nucleotides of probes ligated to duplexes starting with initializing oligonucleotides $i_2$, $i_3$, $i_4$, and so on, will be complementary to the third, fourth, and fifth nucleotides of unknown sequence (50).

In the above embodiment, the oligonucleotide probes are labeled so that the identity of the nucleotide abutting the extended duplex can be determined from the label.

Binding region (40) has a known sequence, but can vary greatly in length and composition. It must be sufficiently long to accommodate the hybridization of an initializing oligonucleotide. Different binding regions can be employed with either identical or different initializing oligonucleotides, but for convenience of preparation, it is preferable to provide identical binding regions and different initializing oligonucleotides. Thus, all the templates are prepared identically and then separated into aliquots for use with different initializing oligonucleotides. Preferably, the binding region should be long enough to accommodate a set of different initializing oligonucleotides, each hydridizing to the template to produce a different starting point for subsequent ligations. Most preferably, the binding region is between about 20 to 50 nucleotides in length.

Initializing oligonucleotides are selected to form highly stable duplexes with the binding region that remain intact during any washing steps of the extension cycles. This is conveniently achieved by selecting the length(s) of the initializing oligonucleotides to be considerably longer than that, or those, of the oligonucleotide probes and/or by selecting them to be GC-rich. Initializing oligonucleotides may also be cross-linked to the template strand by a variety of techniques, e.g. Summerton et al, U.S. Pat. No. 4,123,610; or they may be comprised of nucleotide analogs that form duplexes of greater stability than their natural counterparts, e.g. peptide nucleic acids, Science, 254:1497–1500 (1991); Hanvey et al, Science, 258: 1481–1485 (1992); and PCT applications PCT/EP92/01219 and PCT/EP92/01220.

Preferably, the length of the initializing oligonucleotide is from about 20 to 30 nucleotides and its composition comprises a sufficient percentage of G's and C's to provide a duplex melting temperature that exceeds those of the oligonucleotide probes being employed by about 10–50° C. More preferably, the duplex melting temperature of the initializing oligonucleotide exceeds those of the oligonucleotide probes by about 20–50° C. The number, N, of distinct initializing oligonucleotides employed in a sequencing operation can vary from one, in the case where a single nucleotide is identified at each cycle, to a plurality whose size is limited only by the size of oligonucleotide probe that can be practically employed. Factors limiting the size of the oligonucleotide probe include the difficulty in preparing mixtures having sufficiently high concentrations of individual probes to drive hybridization reactions at a reasonable rate, the susceptibility of longer probes to forming secondary structures, reduction in sensitivity to single base mismatches, and the like. Preferably, N is in the range of from 1 to 16; more preferably, N is in the range of from 1 to 12; and most preferably, N is in the range of from 1 to 8.

A wide variety of oligonucleotide probes can be used with the invention. Generally, the oligonucleotide probes should be capable of being ligated to an initializing oligonucleotide or extended duplex to generate the extended duplex of the next extension cycle; the ligation should be template-driven in that the probe should form a duplex with the template prior to ligation; the probe should possess a blocking moiety to prevent multiple probe ligations on the same template in a single extension cycle, the probe should be capable of being treated or modified to regenerate an extendable end after ligation, and the probe should possess a signaling moiety that permits the acquisition of sequence information relating to the template after a successful ligation. As described more fully below, depending on the embodiment, the extended duplex or initializing oligonucleotide may be extended in either the 5'→3' direction or the 3'→5' direction by oligonucleotide probes. Generally, the oligonucleotide probe need not form a perfectly matched duplex with the template, although such binding is usually preferred. In preferred embodiments in which a single nucleotide in the template is identified in each extension cycle, perfect base pairing is only required for identifying that particular nucleotide. For example, in embodiments where the oligonucleotide probe is enzymatically ligated to an extended duplex, perfect base pairing—ie. proper Watson-Crick base pairing—is required between the terminal nucleotide of the probe which is ligated and its complement in the template. Generally, in such embodiments, the rest of the nucleotides of tie probe serve as "spacers" that ensure the next ligation will take place at a predetermined site, or number of bases, along the template. That is, their pairing, or lack thereof, does not provide further sequence information. Likewise, in embodiments that rely on polymerase extension for base identification, the probe primarily serves as a spacer, so specific hybridization to the template is not critical, although it is desirable.

Preferably, the oligonucleotide probes are applied to templates as mixtures comprising oligonucleotides of all possible sequences of a predetermined length The complexity of such mixtures can be reduced by a number of methods, including using so-called degeneracy-reducing analogs, such as deoxyinosine and the like, e.g. as taught by Kong Thoo Lin et al, Nucleic Acids Research, 20: 5149–5152; U.S. Pat. No. 5,002,867; Nichols et al, Nature, 369: 492–493 (1994); or by separately applying multiple mixtures of oligonucleotide probes, e.g. four mixtures comprising four disjoint subsets of oligonucleotide sequences that taken together would comprise all possible sequences of the predetermined length.

Initializing oligonucleotides and oligonucleotide probes of the invention are conveniently synthesized on an automated DNA synthesizer, e.g. an Applied Biosystems, Inc. (Foster City, Calif.) model 392 or 394 DNA/RNA Synthesizer, using standard chemistries, such as phosphoramidite chemistry, e.g. disclosed in the following references: Beaucage and Iyer, Tetrahedron, 48: 2223–2311 (1992); Molko et al, U.S. Pat. No. 4,980,460; Koster et al, U.S. Pat. No. 4,725,677; Caruthers et al, U.S. Pat. Nos. 4,415,732; 4,458,066; and 4,973,679; and the like. Alternative chemistries, e.g. resulting in non-natural backbone groups, such as phosphorothioate, phosphoramidate, and the like, may also be employed provided that the resulting oligonucleotides are compatible with the ligation and other reagents of a particular embodiment Mixtures of oligonucleotide probes are readily synthesized using well known techniques, e.g. as disclosed in Telenius et al, Genomics, 13: 718–725 (1992); Welsh et al, Nucleic Acids Research, 19: 5275–5279 (1991); Grothues et al, Nucleic Acids Research, 21: 1321–1322 (1993); Hartley, European patent application 90304496.4; and the like. Generally, these techniques simply call for the application of mixtures of the activated monomers to the growing oligonucleotide during the coupling steps where one desires to introduce the degeneracy.

When conventional ligases are employed in the invention, as described more fully below, the 5' end of the probe may be phosphorylated in some embodiments. A 5' monophosphate can be attached to an oligonucleotide either chemically or enzymatically with a kinase, e.g. Sambrook et al, Molecular Cloning: A Laboratory Manual, 2nd Edition (Cold Spring Harbor Laboratory, New York, 1989). Chemical phosphorylation is described by Horn and Urdea, Tetrahedron Lett, 27: 4705 (1986), and reagents for carrying out the disclosed protocols are commercially available, e.g. 5' Phosphate-ON™ from Clontech Laboratories (Palo Alto, Calif.). Preferably, when required, oligonucleotide probes are chemically phosphorylated.

The probes of the invention can be labeled in a variety of ways, including the direct or indirect attachment of fluorescent moieties, colorimetric moieties, and the like. Many comprehensive reviews of methodologies for labeling DNA and constructing DNA probes provide guidance applicable to constructing probes of the present invention. Such reviews include Matthews et al, Anal. Biochem., Vol 169, pgs. 1–25 (1988); Haugland, Handbook of Fluorescent Probes and Research Chemicals Molecular Probes, Inc., Eugene, 1992); Keller and Manak, DNA Probes, 2nd Edition (Stockton Press, New York, 1993); and Eckstein, editor, Oligonucleotides and Analogues: A Practical Approach (IRL Press, Oxford, 1991); and the like. Many more particular methodologies applicable to the invention are disclosed in the following sample of references: Fung et al, U.S. Pat. No. 4,757,141; Hobbs, Jr., et al U.S. Pat. No. 5,151,507; Cruickshank, U.S. Pat. No. 5,091,519; (synthesis of functionalized oligonucleotides for attachment of reporter groups); Jablonski et al, Nucleic Acids Research, 14: 6115–6128 (1986)(enzyme-oligonucleotide conjugates); and Urdea et al, U.S. Pat. No. 5,124,246 (branched DNA).

Preferably, the probes are labeled with one or more fluorescent dyes, e.g. as disclosed by Menchen et al, U.S. Pat. No. 5,188,934; Begot et al PCT application PCT/US90105565.

Guidance in selecting hybridization conditions for the application of oligonucleotide probes to templates can be found in numerous references, e.g. Wetmur, Critical Reviews in Biochemistry and Molecular Biology, 26: 227–259 (1991); Dove and Davidson, J. Mol. Biol. 5: 467–478 (1962); Hutton, Nucleic Acids Research, 10: 3537–3555 (1977); Breslauer et al, Proc. Natl. Acad. Sci. 83: 3746–3750 (1986); innis et al, editors, PCR Protocols (Academic Press, New York, 1990); and the like.

Generally, when an oligonucleotide probe anneals to a template in juxtaposition to an end of the extended duplex, the duplex and probe are ligated, i.e. are caused to be covalently linked to one another. Ligation can be accomplished either enzymatically or chemically. Chemical ligation methods are well known in the art, e.g. Ferris et al, Nucleosides & Nucleotides, 8: 407–414 (1989); Shabarova et al, Nucleic Acids Research, 19: 4247–4251 (1991); and the like. Preferably, enzymatic ligation is carried out using a ligase in a standard protocol. Many ligases are known and are suitable for use in the invention, e.g. Lehman, Science, 186: 790–797 (1974); Engler et al, DNA Ligases, pages 3–30 in Boyer, editor, The Enzymes, Vol. 15B (Academic Press, New York, 1982); and the like. Preferred ligases include T4 DNA ligase, T7 DNA ligase, E. coli DNA ligase, Taq ligase, Pfu ligase, and Tth ligase. Protocols for their use are well known, e.g. Sambrook et al (cited above); Barany, PCR Methods and Applications, 1: 5–16 (1991); Marsh et al, Strategies, 5: 73–76 (1992); and the like. Generally, ligases require that a 5' phosphate group be present for ligation to the 3' hydroxyl of an abutting strand.

Preparing Target Polynucleotides

Preferably, a target polynucleotide is conjugated to a binding region to form a template, and the template is attached to a solid phase support, such as a magnetic particle, polymeric microsphere, filter material, or the like, which permits the sequential application of reagents without complicated and time-consuming purification steps. The length of the target polynucleotide can vary widely; however, for convenience of preparation, lengths employed in conventional sequencing are preferred. For example, lengths in the range of a few hundred basepairs, 200–300, to 1 to 2 kilobase pairs are preferred.

The target polynucleotides can be prepared by various conventional methods. For example, target polynucleotides can be prepared as inserts of any of the conventional cloning vectors, including those used in conventional DNA sequencing. Extensive guidance for selecting and using appropriate cloning vectors is found in Sambrook et al, Molecular Cloning: A Laboratory Manual, Second Edition (Cold Spring Harbor Laboratory, New York, 1989), and like references. Sambrook et al and Innis et al, editors, PCR Protocols (Academic Press, New York, 1990) also provide guidance for using polymerase chain reactions to prepare target polynucleotides. Preferably, cloned or PCR-amplified target polynucleotides are prepared which permit attachment to magnetic beads, or other solid supports, for ease of separating the target polynucleotide from other reagents used in the method. Protocols for such preparative techniques are described fully in Wahlberg et al, Electrophoresis, 13: 547–551 (1992); Tong et al, Anal. Chem., 64: 2672–2677 (1992); Hultman et al, Nucleic Acids Research, 17: 4937–4946 (1989); Hultman et al, Biotechniques, 10: 84–93 (1991); Syvanen et al, Nucleic Acids Research, 16: 11327–11338 (1988); Dattagupta et al, U.S. Pat. No. 4,734, 363; Uhlen, PCT application PCT/GB89/00304; and like references. Kits are also commercially available for practicing such methods, e.g. Dynabeads™ template preparation kit from Dynal AS. (Oslo, Norway).

Generally, the size and shape of a microparticle or beads employed in the method of the invention is not critical; however, microparticles in the size range of a few, e.g. 1–2, to several hundred, e.g. 200–1000 µm diameter are preferable, as they minimize reagent and sample usage while permitting the generation of readily detectable signals, e.g. from fluorescently labeled probes.

Schemes for Ligating, Capping, and Regenerating Extendable Termini

In one aspect, the invention calls for repeated steps of ligating and identifying of oligonucleotide probes. However, since the ligation of multiple probes to the same extended duplex in the same step would usually introduce identification problems, it is useful to prevent multiple extensions and to regenerate extendable termini. Moreover, if the ligation step is not 100% efficient, it would be desirable to cap extended duplexes that fail to undergo ligation so that they do not participate in any further ligation steps. That is, a capping step preferably occurs after a ligation step, by analogy with other synthetic chemical processes, such as polynucleotide synthesis, e.g. Andrus et al, U.S. Pat. No. 4,816,571. This would remove a potentially significant source of noise from signals generated in subsequent identification steps.

Below, several exemplary schemes for carrying out ligation, capping, regeneration, and identification steps in accordance with the invention are described. They are presented for purposes of guidance and are not meant to be limiting.

Figure 2:
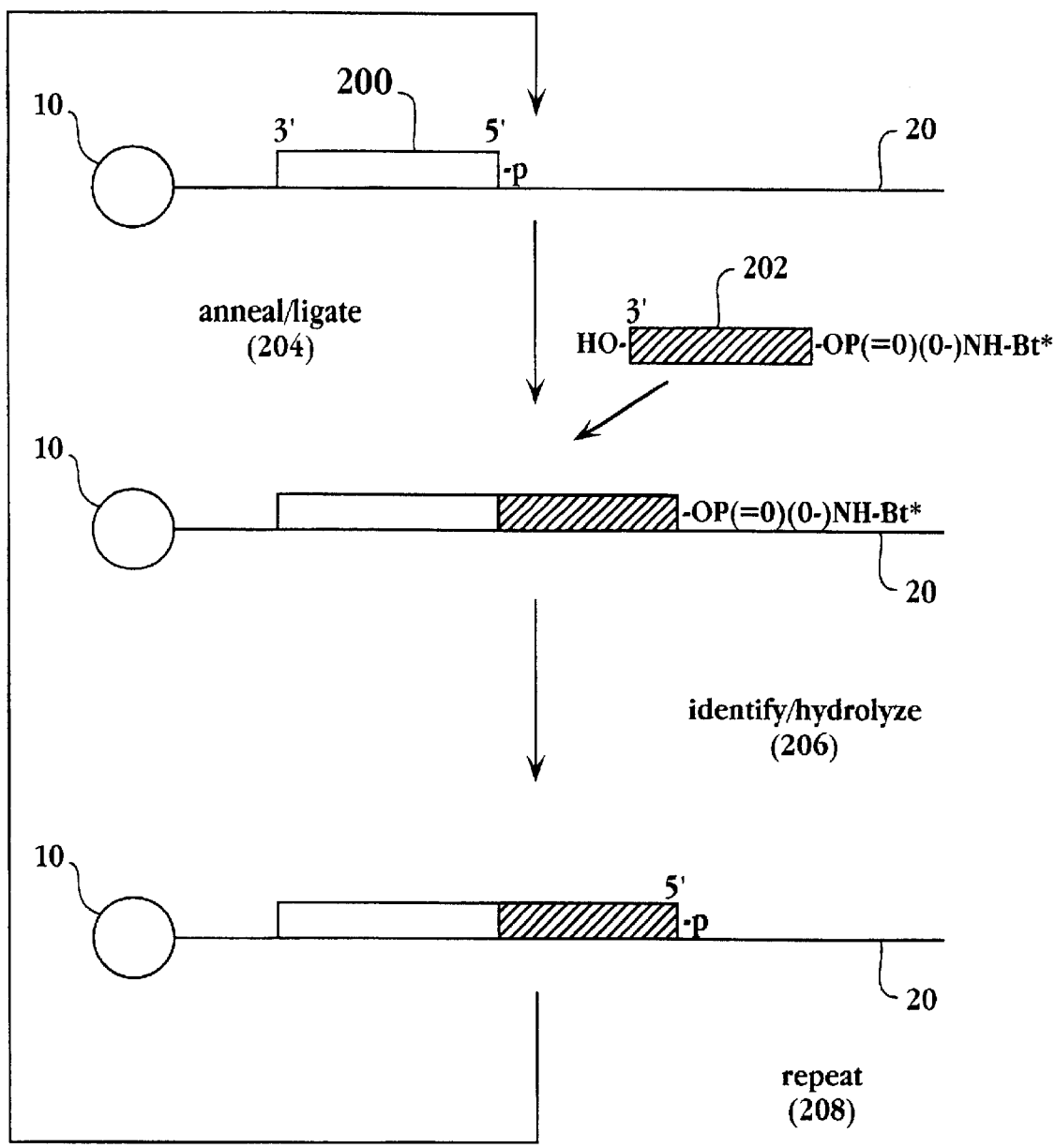
FIG. 2 diagrammatically illustrates an embodiment of the invention employing acid-labile linkages.

A scheme for extending an initializing oligonucleotide or an extended duplex in the 3'→5' direction is illustrated in FIG. 2. Template (20) is attached to solid phase support (10) by its 5' end. This can be conveniently accomplished via a biotin, or like linking moiety, using conventional techniques. Initializing oligonucleotide (200) having a 5' phosphate group is annealed to template (20) as described above prior to the initial cycle of ligation and identification. An oligonucleotide probe (202) of the following form is employed:

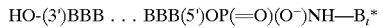

HO-(3')BBB ... BBB(5')OP(=O)(O⁻)NH—B$_t$* where BBB ... BBB represents the sequence of nucleotides of oligonucleotide probe (202) and B$_t$* is a labeled chain-terminating moiety linked to the 5' carbon of the oligonucleotide via a phosphoramidate group, or other labile linkage, such as a photocleavable linkage. The nature of B$_t$* may vary widely. It can be a labeled nucleoside (e.g. coupled via a 5'P→3'N phosphoramidate) or other moiety, so long as it prevents successive ligations. It may simply be a label connected by a linker, such as described in Agrawal and Tang, International application number PCT/US91/08347. An important feature of the oligonucleotide probe is that after annealing and ligation (204), the label may be removed and the extendable end regenerated by treating the phosphoramidate linkage with acid, e.g. as taught by Letsinger et al, J. Am. Chem. Soc., 94: 292–293 (1971); Letsinger et al, Biochem., 15: 2810–2816 (1976); Gryaznov et al, Nucleic Acid Research, 20: 3403–3409 (1992); and like references. By way of example, hydrolysis of the phosphoramidate may be accomplished by treatment with 0.8% trifluoroacetic acid in dichloromethane for 40 minutes at room temperature. Thus, after annealing, ligating, and identifying the ligated probe via the label on B$_t$*, the chain-terminating moiety is cleaved by acid hydrolysis (206) thereby breaking the phosphorus linkage and leaving a 5' monophosphate on the ligated oligonucleotide. The steps can be repeated (208) in successive cycles. In one aspect of this embodiment, a single initializing oligonucleotide may be employed such that only one nucleotide is identified in each sequencing cycle. For such an embodiment, the above probe preferably has the following form:

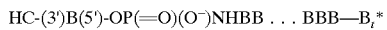

HC-(3')B(5')-OP(=O)(O⁻)NHBB ... BBB—B$_t$*

Thus, after each ligation step and acid cleavage step the duplex will be extended by one nucleotide.

A capping step may be introduced prior to hydrolysis. For example, probe (202) may have the form:

HO-(3')BB ... Bp^B ... BB(5')-OP(=O)(O⁻)NH—B$_t$* where "p^" is a exonuclease resistant linkage, such as phosphorothioate, methylphosphonate, or the like. In such an embodiment, capping can be achieved by treating tie extended duplexes with an exonuclease, such as λ exonuclease, which will cleave the unligated extended duplexes back to the exonuclease resistant linkage. The presence of this linkage at the 5' end of the extended duplex will then prevent it from participating in subsequent ligations. Clearly, many other capping methodologies may be employed, e.g. acylation, ligation of an inert oligonucleotide, or the like. When free 3' hydroxyls are involved, capping may be accomplished by extending the duplex with a DNA polymerase in the presence of chain-terminating nucleoside triphosphates, e.g. dideoxynucleoside triphosphates, or the like.

The phosphoramidate linkage described above is an example of a general class of internucleosidic linkages referred to herein as "chemically scissile internucleosidic linkages." These are internucleosidic linkages that may be cleaved by treating them with characteristic chemical or physical conditions, such as an oxidizing environment, a reducing environment, light of a characteristic wavelength (for photolabile linkages), or the like. Other examples of chemically scissile internucleosidic linkages which may be used in accordance with the invention are described in Urdea U.S. Pat. No. 5,380,833; Gryaznov et al, Nucleic Acids Research, 21: 1403–1408 (1993)(disulfide); Gryaznov et al, Nucleic Acids Research, 22: 2366–2369 (1994) (bromoacetyl); Urdea et al, International application PCT/US91/05287 (photolabile); and like references.

Further chemically scissile linkages that may be employed with the invention include chain-terminating nucleotides that may be chemically converted into an extendable nucleoside. Examples of such compounds are described in the following references: Canard et al, international application number PCT/FR400345; Ansorge, German patent application No. DE 4141178 A1; Metzker et al, Nucleic Acids Research, 22: 4259–4267 (1994); Cheeseman, U.S. Pat. No. 5,302,509; Ross et al, International application PCT/US90/06178; and the like.

Figure 3A:
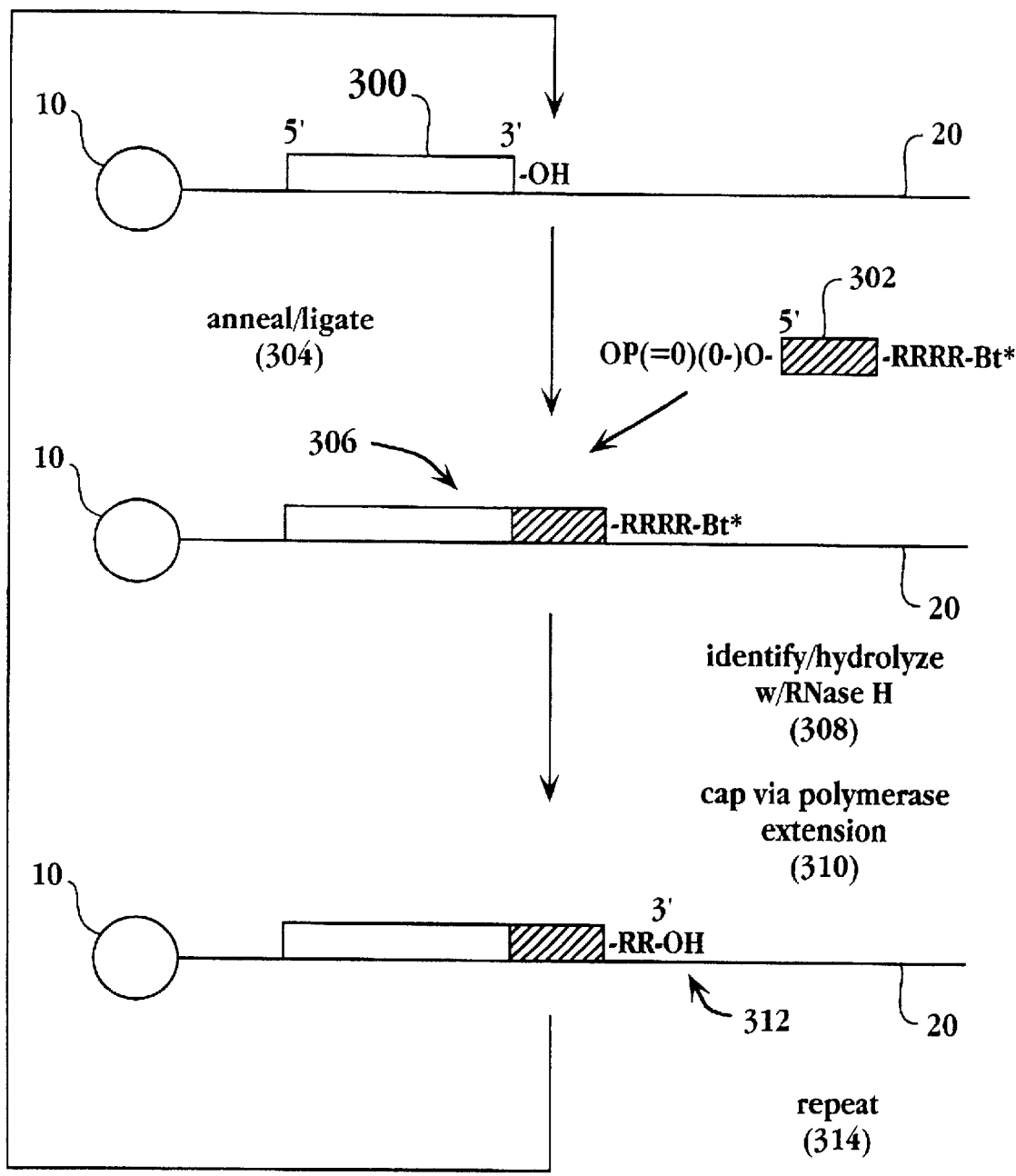
FIG. 3A diagrammatically illustrates an embodiment of the invention employing RNase H labile oligonucleotides with 3'→5' extensions.

A scheme for extending an initializing oligonucleotide or an extended duplex in the 5'→3' direction is illustrated in FIG. 3A. Template (20) is attached to solid phase support (10) by its 3' end. As above, this can be conveniently accomplished via a biotin, or like linking moiety, using conventional techniques. Initializing oligonucleotide (300) having a 3' hydroxy group is annealed to template (20) as described above prior to the initial cycle of ligation and identification. An oligonucleotide probe (302) of the following form is employed:

OP(=O)(O⁻)O-(5')BBB ... BBBRRRRB$_t$* where BBB ... BBBRRRR represents the sequence of 2'-deoxynucleotides of oligonucleotide probe (302), "RRRR" represent a sequence of four ribonucleotides of probe (302), and B$_t$* is a labeled chain-terminating moiety, as described above. Such mixed RNA-DNA oligonucleotides are readily synthesized using conventional automated DNA synthesizers, e.g. Duck et al, U.S. Pat. No. 5,011,769. RNase H will cleave the probe specifically in the center of the four ribonucleotide segment, Hogrefe et al, J. Biol. Chem., 265: 5561–5566 (1990), leaving a 3' hydroxyl (312) on the extended duplex, which may participate in subsequent ligation steps. Thus, a cycle in the present embodiment proceeds by annealing probe (302) to template (20) and ligating (304) to form extended duplex (306). After identification via B$_t$*, the extended duplex is treated with RNase H to cleave the label and regenerate an extendable end. The cycle is then repeated (314). Capping (310) can be carried out prior to RNase H treatment by extending the unligated ends with a DNA polymerase in the presence of the four dideoxynucleoside triphosphates, ddATP ddCIP, ddGTP, and ddTTP.

Figure 3B:
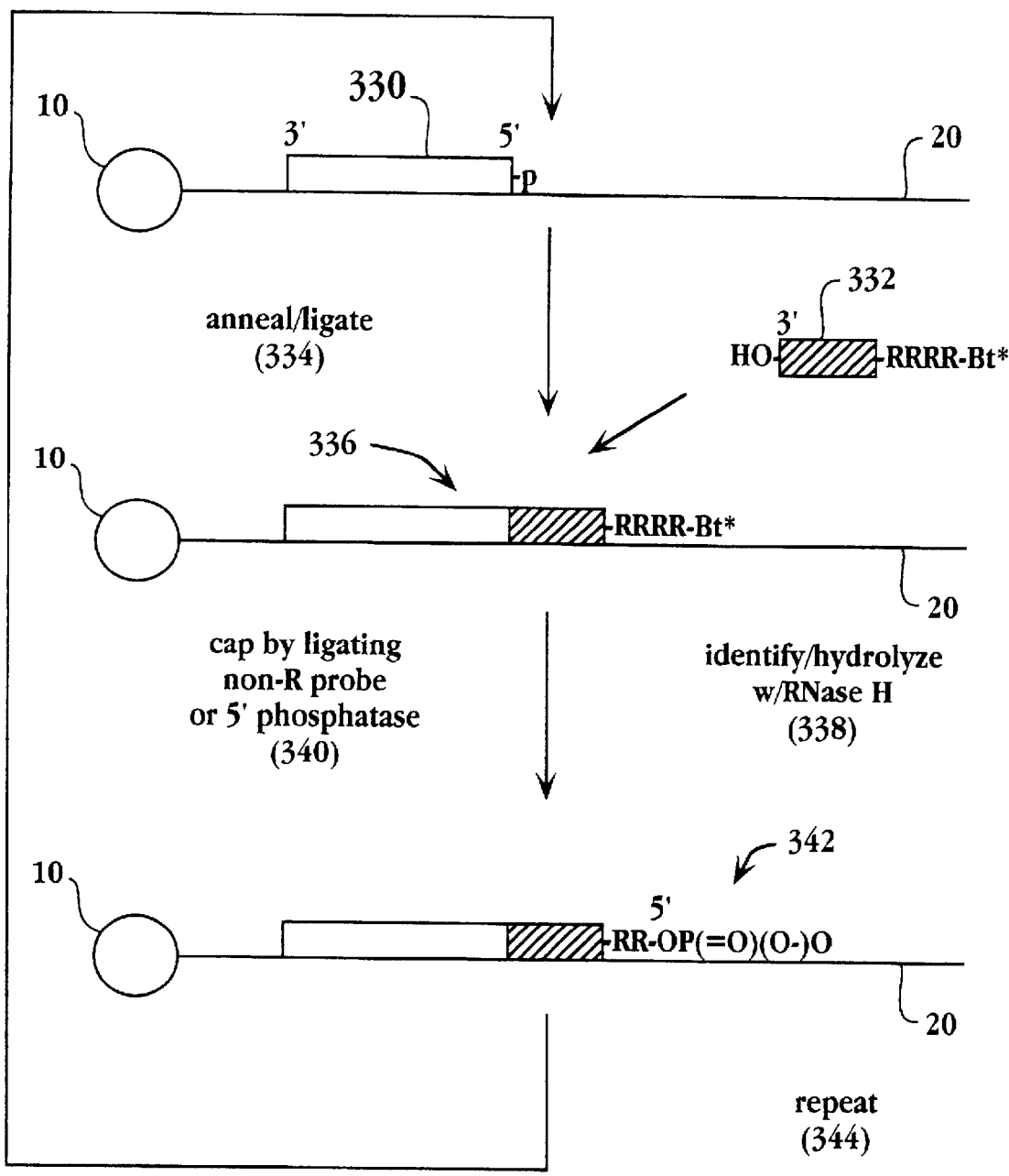
FIG. 3B diagrammatically illustrates an embodiment of the invention employing RNase H labile oligonucleotides with 3'→5' extensions.

As illustrated in FIG. 3B, a similar scheme can be employed for 3'→5' extensions. In such an embodiment, initiating oligonucleotide or extended duplex (330) has a 5' monophosphate and the oligonucleotide probe (332) has the form:

HO-(3')BBB . . . BBBRRRRB . . . BB$_t$*

As above, after annealing, ligating (334), and identifying (338), extended duplex (336) is cleaved by RNase H which in this case leaves a 5' monophosphate (342) at the terminus of the extended duplex. With the regenerated extendable end, the cycle can be repeated (344). A capping step can be included prior to RNase H hydrolysis by either ligating an unlabeled non-RNA-containing probe, or by removing any remaining 5' monophosphates by treatment with a phosphatase.

Figure 4:
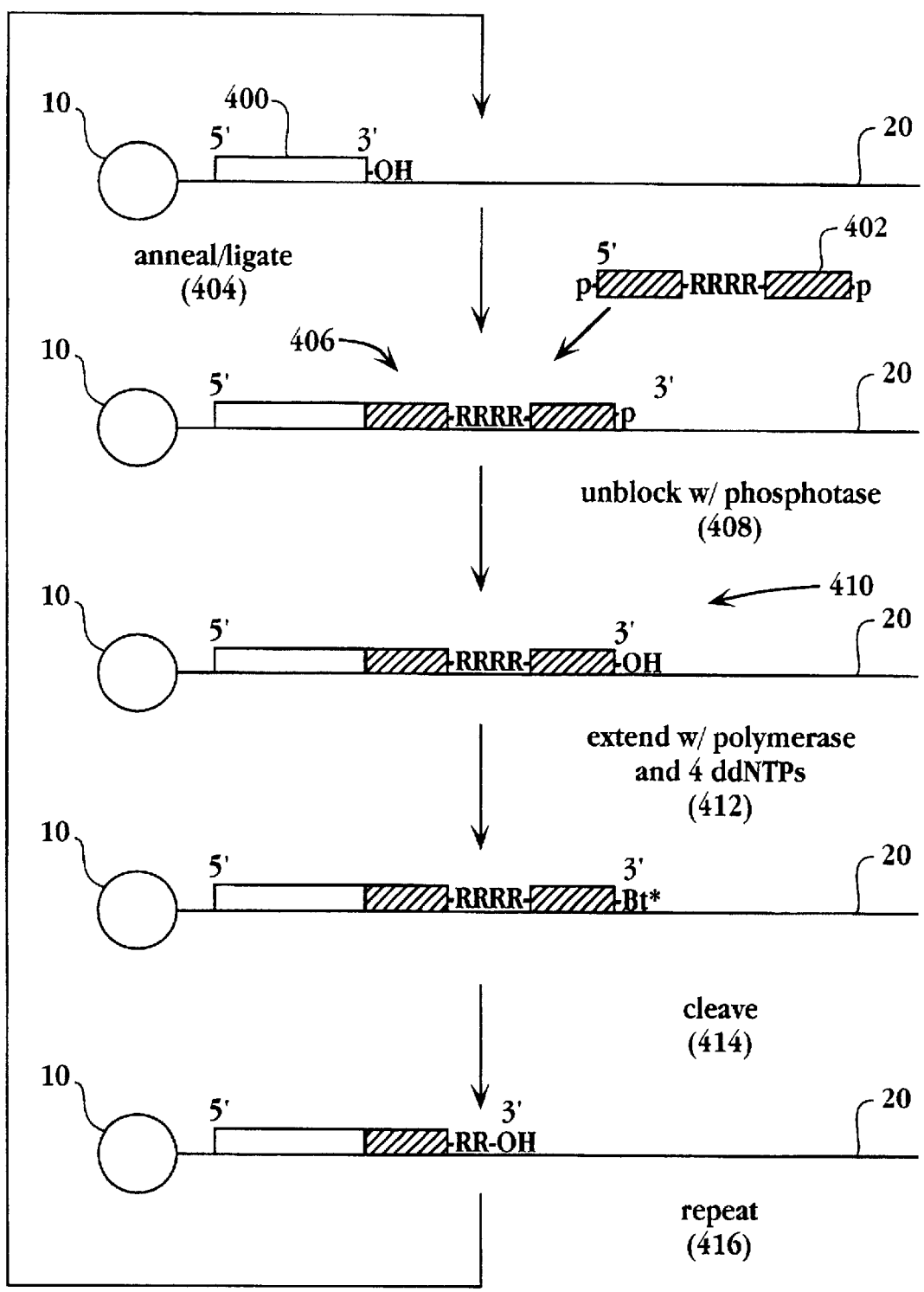
FIG. 4 diagrammatically illustrates an embodiment of the invention employing ligation followed by polymerase extension and cleavage.

Identification of nucleotides can be accomplished by polymerase extension following ligation. As exemplified in FIG. 4, for this embodiment, template (20) is attached to solid phase support (10) as described above and initializing oligonucleotide (400) having a 3' hydroxyl is annealed to the template prior to the initial cycle. Oligonucleotide probes (402) of the form:

OP(=O)(O$^-$)O(5')BBB . . . BBBRRRRB . . . B(3')OP(=O)(O$^-$)O are annealed to template (20) and ligated (404) to form extended duplex (406). The 3' monophosphate, which prevents successive ligations of probes in the same cycle, is removed with phosphatase (408) to expose a free 3' hydroxyl (410). Clearly, alternative blocking approaches may also be used. Extended duplex (406) is further extended by a nucleic acid polymerase in the presence of labeled dideoxynucleoside triphosphates (412), thereby permitting the identification of a nucleotide of template (20) by the label of the incorporated dideoxynucleotide. The labeled dideoxynucleotide and a portion of probe (402) are then cleaved (414), for example, by RNase H treatment, to regenerate an extendable end on extended duplex (406). The cycle is then repeated (416).

In order to reduce the number of separate annealing reactions that must be carried out, the oligonucleotide probes may be grouped into mixtures, or subsets, of probes whose perfectly matched duplexes with complementary sequences have similar stability or free energy of binding. Such subsets of oligonucleotide probes having similar duplex stability are referred to herein as "stringency classes" of oligonucleotide probes. The mixtures, or stringency classes, of oligonucleotide probes are then separately combined with the target polynucleotide under conditions such that substantially only oligonucleotide probes complementary to the target polynucleotide form duplexes. That is, the stringency of the hybridization reaction is selected so that substantially only perfectly complementary oligonucleotide probes form duplexes. These perfectly matched duplexes are then ligated to form extended duplexes. For a given oligonucleotide probe length, the number of oligonucleotide probes within each stringency class can vary widely. Selection of oligonucleotide probe length and stringency class size depends on several factors, such as length of target sequence and how it is prepared, the extent to which the hybridization reactions can be automated, the degree to which the stringency of the hybridization reaction can be controlled, the presence or absence of oligonucleotide probes with complementary sequences, and the like. Guidance in selecting an appropriate size of stringency class for a particular embodiment can be found in the general literature on nucleic acid hybridization and polymerase chain reaction methodology, e.g. Gotoh, Adv. Biophys. 16: 1–52 (1983); Wetmer, Critical Reviews in Biochemistry and Molecular Biology 26: 227–259 (1991); Breslauer et al, Proc. Natl. Acad. Sci. 83: 3746–3750 (1986); Wolf et al, Nucleic Acids Research, 15: 2911–2926 (1987); Innis et al, editors, PCR Protocols (Academic Press, New York, 1990); McGraw et al, Biotechniques, 8: 674–678 (1990), and the like. Stringency can be controlled. several varying several parameters, including temperature, salt concentration, concentration of certain organic solvents, such as formamide, and the like. Preferably, temperature is used to define the stringency classes because the activity of the various polymerases or ligases employed limits the degree to which salt concentration or organic solvent concentration can be varied for ensuring specific annealing of the oligonucleotide probes.

Generally, the larger the stringency class the greater the complexity of the hybridizing mixture and the lower the concentration of any particular oligonucleotide probe in the mixture. A lower concentration of a oligonucleotide probe having a complementary site on a target polynucleotide reduces the relative likelihood of the oligonucleotide probe hybridizing and being ligated This, in turn, lead to reduced sensitivity. Larger stringency classes also have a greater variance in the stabilities of the duplexes that form between a oligonucleotide probe and a complementary sequence. On the other hand, smaller stringency classes require a larger number of hybridization reactions to ensure that all oligonucleotide probes of a set are hybridized to a target polynucleotide.

For example, when 8-mer oligonucleotide probes are employed stringency classes may include between about 50 to about 500 oligonucleotide probes each. Thus, several hundred to several thousand hybridization ligation reactions are required For larger sized oligonucleotide probes, much larger stringency classes are required to make the number of hybridization/extension reactions practical, e.g. $10^4$–$10^5$, or more.

Oligonucleotide probes of the same stringency class can be synthesized simultaneously, in a manner similar to which fully random oligonucleotide probes are synthesized, e.g. as disclosed in Telenius et al, Genomics, 13: 718–725 (1992); Welsh et al, Nucleic Acids Research, 19: 5275–5279 (1991); Grothues et al, Nucleic Acids Research, 21: 1321–1322 (1993); Hartley, European patent application 90304496.4; and the like. The difference is that at each cycle different mixtures of monomers are applied to the growing oligonucleotide probe chain, wherein the proportion of each monomer in the mixture is dictated by the proportion of each nucleoside at the position of the oligonucleotide probe in the stringency class. Stringency classes are readily formed by computing the free energy of duplex formation by available algorithms, e.g. Breslauer et al, Proc. Natl. Acad. Sci., 83: 3746–3750 (1986); Lowe et al, Nucleic Acids Research, 18: 1757–1761 (1990), or the like. The oligonucleotide probes can be ordered according to the free energy of binding to their complement under standard reaction conditions, e.g. with a standard bubble sort, Baase, Computer Algorithms (Addison-Wesley, Menlo Park, 1978). For example the following is the list of ten 6-mers, with the greatest stability (from top to bottom) in terms of free energy of duplex formation under standard hybridization conditions and the least stability in terms of free energy of duplex formation (the free energies being computed via Breslauer (cited above)):

| Ranking | Oligonucleotide probe Sequence(5' → 3') |
|---|---|
| 1 | GCGCGC |
| 2 | CGCGCG |
| 3 | CCCGCG |
| 4 | CGCCCG |
| 5 | CGCGCC |
| 6 | CGCGGC |
| 7 | CGGCGC |
| 8 | GCCGCG |
| 9 | GCGCCG |
| 10 | GCGCGG |
| . | . |
| . | . |
| . | . |
| 4087 | TCATAT |
| 4088 | TGATAT |
| 4089 | CATATA |
| 4090 | TATATG |
| 4091 | ATCATG |
| 4092 | ATGATG |
| 4093 | CATCAT |
| 4094 | CATGAT |
| 4095 | CATATG |
| 4096 | ATATAT |

Thus, if a stringency class consisted of the first ten 6-mers the mixture of monomers for the first (3'-most) position would be 0:4:6:0 (A:C:G:T), for the second position it would be 0:6:4:0, and so on. If a stringency class consisted of the last ten 6-mers, the mixture of monomers for the first position would be 1:0:4:5, for the second position it would be 5:0:0:5, and so on. The resulting mixtures may then be further enriched for sequences of the desired stringency class by thermal elution, e.g. Miyazawa et al, J. Mol. Biol., 11: 223–237 (1965).

More conveniently, stringency classes containing several hundred to several thousands of oligonucleotides may be synthesized directly by a variety of parallel synthesis approaches, e.g. Frank et al, U.S. Pat. No. 4,689,405; Matson et al, Anal. Biochem., 224: 110–116 (1995); Fodor et al, International application PCT/US93/04145; Pease et al, Proc. Natl. Acad. Sci., 91: 5022–5026 (1994); Southern et al, J. Biotechnology, 35: 217–227 (1994), Brennan, International application PCT/US94/05896; or the like.

In some cases it may be desirable to form additional stringency classes of oligonucleotide probes by placing in a separate subset oligonucleotide probes having complementary sequences to other oligonucleotide probes in a subset or oligonucleotide probes that are susceptible of forming oligonucleotide probe-dimers.

Clearly, one of ordinary skill in the art could combine features of the embodiments set forth above to design still further embodiments in accordance with the invention, but not expressly set forth above.

The invention also includes systems and apparatus for carrying out the method of the invention automatically. Such systems and apparatus can take a variety of forms depending on several design constraints, including i) the nature of the solid phase support used to anchor the target polynucleotide, ii) the degree of parallel operation desired, iii) the detection scheme employed; iv) whether reagents are reused or discarded, and the like. Generally, the apparatus comprises a series of reagent reservoirs, one or more reaction vessels containing target polynucleotide, preferably attached to a solid phase support, e.g. magnetic beads, one or more detection stations, and a computer controlled means for transferring in a predetermined manner reagents from the reagent reservoirs to and from the reaction vessels and the detection stations. The computer controlled means for transferring reagents and controlling temperature can be implemented by a variety of general purpose laboratory robots, such as that disclosed by Harrison et al, Biotechniques, 14: 88–97 (1993); Fujita et al, Biotechniques, 9: 584–591 (1990); Wada et al, Rev. Sci. Instrum., 54: 1569–1572 (1983); or the like. Such laboratory robots are also available commercially, e.g. Applied Biosystems model 800 Catalyst (Foster City, Calif.).

A variety of kits may be provided for carrying out different embodiments of the invention. Generally, kits of the invention include oligonucleotide probes, initializing oligonucleotides, and a detection system. Kits further include ligation reagents and instructions for practicing the particular embodiment of the invention. In embodiments employing protein ligases, RNase H, nucleic acid polymerases, or other enzymes, their respective buffers may be included. In some cases, these buffers may be identical. Preferably, kits also include a solid phase support, e.g. magnetic beads, for anchoring templates. In one preferred kit, fluorescently labeled oligonucleotide probes are provided such that probes corresponding to different terminal nucleotides of the target polynucleotide carry distinct spectrally resolvable fluorescent dyes. As used herein, "spectrally resolvable" means that the dyes may be distinguished on basis of their spectral characteristics, particularly fluorescence emission wavelength, under conditions of operation. Thus, the identity of the one or more terminal nucleotides would be correlated to a distinct color, or perhaps ratio of intensities at different wavelengths. More preferably, four such probes are provided that allow a one-to-one correspondence between each of four spectrally resolvable fluorescent dyes and the four possible terminal nucleotides on a target polynucleotide. Sets of spectrally resolvable dyes are disclosed in U.S. Pat. Nos. 4,855,225 and 5,188,934; International application PCT/US90/05565; and Lee et al, Nucleic Acids Researchs, 20: 2471–2483 (1992).

EXAMPLE 1

Sequencing a Target Polynucleotide Amplified from pUC19 with Four Initializing Oglionucleotides In this example, a template comprising a binding region and a portion of the pUC19 plasmid is amplified by PCR and attached to magnetic beads. Four initializing oligonucleotides are employed in separate reactions as indicated below. 8-mer oligonucleotide probes are employed having 4 central ribonucleotides and both 5' and 3' monophosphates, as shown in the following formula:

OP(=O)(O⁻)O-(5)BBRRRRBB(3)OP(=O)(O⁻)O

After annealing, probes are enzymatically ligated to the initializing oligonucleotides and the magnetic bead supports are washed. The 3' phosphates of the ligated probes are removed with phosphatase, after which the probes are extended with DNA polymerase in the presence of the four labeled dideoxynucleoside triphosphate chain terminators. After washing and identification of the extended nucleotide, the ligated probes are cleaved at the ribonucleotide moiety with RNAse H to remove the label and to regenerate an extendable end.

The following double stranded fragment comprising a 36-mer binding region is ligated into a Sac I/Sma I-digested pUC19 (upper strand: SEQ ID NO:1; lower strand: SEQ ID NO:9):

CCTCTCCCTTCCCTCTCCTCCCTCTC-
CCCTCTCCCTC TCGAGGAGAGGGAAGG-
GAGAGGAGGGAGAGGGGAGAGGGAGGGCC

After isolation and amplification, a 402 basepair fragment of the modified pUC19 is amplified by PCR for use as a template. The fragment spans a region of pUC19 from position 41 to the binding region inserted adjacent to the Sac I site in the polylinker region (position 413 of the unmodified pUC 19), Yanisch-Perron et al, Gene, 33: 103–119 (1985). Two 18-mer oligonucleotide probes are employed having sequences 5'-CCCTCTCCCCTCTCCTCx-3' (SEQ. ID:10) and 5'-GCAGCTCCCGGAGACGGT-3', (SEQ. ID:11) where "x" is a 3' biotin moiety attached during synthesis using a commercially available reagent with manufacturer's protocol, e.g. 3' Biotin-ON CPG (Clontech Laboratories, Palo Alto, Calif.). The amplified template is isolated and attached to streptavidin-coated magnetic beads (Dynabeads) using manufacturer's protocol, Dynabeads Template Preparation Kit, with M280-Streptavidin (Dynal, Inc., Great Neck, N.Y.). A sufficient quantity of the biotinylated 313 basepair fragment is provided to load about 300 µg of Dynabeads M280-Streptavidin.

The binding region sequence is chosen so that the duplexes formed with the initiating oligonucleotides have compositions of about 66% GC to enhance duplex stability. The sequence is also chosen to prevent secondary structure formation and fortuitous hybridization of an initializing oligonucleotide to more than one location within the binding region. Any shifting of position of a given initializing oligonucleoide within the binding region results in a significant number of mismatched bases.

After loading, the non-biotinylated strand of template is removed by heat denaturation, after which the magnetic beads are washed and separated into four aliquots. The template attached to the magnetic beads has the following sequence, where the defined sequences separated by the ellipses ( . . . ) are listed in the attached sequence listing as two separate sequences, SEQ ID NO:12 and SEQ ID NO:13:

(Magnetic bead)-(linker)-(3')-CTCCCTCTCCCCTCTCCCTCCTC TCCCTTC-CTCTCCTCGACTTAAGT . . . CTCGACG-(5')

The following four oligonucleotides are employed as initializing oligonucleolides in each of the separate aliquots of template:

(SEQ ID:2) 5'-GAGGAGAGGGAAGGAGAGGAG
(SEQ ID:3) 5'-GGAGGAGAGGGAAGGAGAGGA
(SEQ ID:4) 5'-GGGAGGAGAGGGAAGGAGAGG
(SEQ ID:5) 5'-AGGGAGGAGAGGGAAGGAGAG

Reactions and washes below are generally carried out in 50 µL volumes of manufacturer's (New England Biolabs) recommended buffers for the enzymes employed, unless otherwise indicated. Standard buffers are also described in Sambrook et al, Molecular Cloning, 2nd Edition (Cold Spring Harbor Laboratory Press, 1989).

96 stingency classes of 684 or 682 oligonucleotide probes each (2 subsets for each of 48 different annealing temperatures) are formed which together contain all 8-mer probes for each of the four aliquots. The probes of each of the 96 classes are separately annealed to the target polynucleotide in reaction mixtures having the same components, with the exception that extensions and ligations carried out with Sequenase and T4 DNA ligase at temperatures less than 37° C. and extensions and ligations carried out with Taq Stoffel fragment and a thermostable ligase otherwise.

The 48 stringency conditions are defined by annealing temperatures which range from 22° C. to 70° C., such that each grouping of subsets at the same temperature differ in annealing temperature by 1° C. from that of the subset groupings containing the next highest and next lowest stringency classes. The range of annealing temperatures (22–70° C.) is roughly bounded by the temperatures 5–10 degrees below the temperatures at which the least stable and most stable 8-mers, respectively, are expected to have about fifty percent maximum annealing in a standard PCR buffer solution.

After 5–10 minutes incubation at 80° C., the reaction mixtures are brought down to their respective annealing temperatures over a period of 20–30 minutes. After ligation, washing and treatment with phosphatase, 2 units of polymerase and labeled dideoxynucleotide triphosphates (0.08 mM final reaction concentration and labeled with TAMRA (tetramethylrhodamine), FAM (fluorescein), ROX (rhodamine X), and JOE (2',7'-dimethoxy4',5'-dichlorofluorescein) are added. After 15 minutes, the beads are washed with $H_2O$ and the identity of the extended nucleotide is determined by illuminating each reaction mixture with standard wavelengths, e.g Users Manual, model 373 DNA Sequencer (Applied Biosystems, Foster City, Calif.).

After identification, the reaction mixtures are treated with RNase H using the manufacturer's suggested protocol and washed. The RNase H treated extended duplexes have regenerated 3' hydroxyls and are ready for the next cycle of ligation/extension/cleavage. The cycles are carried out until all the nucleotides of the test sequence are identified.

EXAMPLE 2

Sequencing a Target Polynucleotide Amplified from pUC 19 with One Initializing Oligonucleotide In this example, a template is prepared in accordance with Example 1, except that since extension is in the 5'→3' direction in this example, the biotin moiety is attached to the 5' end of the primer hybridizing to the CT-rich strand of the binding region. Thus, in this example, the binding region of the single stranded template will be a GA-rich segment (essentially the complement of the binding region of Example 1). Two 18-mer oligonucleotide probes are employed having sequences 5'-xGAGGGAGAGGGGAGAGGG-3' (SEQ. ID:6) and 5'-ACCGTCTCCGGGAGCTGC-3', (SEQ. ID:7), where "x" is a 5' biotin moiety is attached during synthesis using commercially available reagents with manufacturers' protocols, e.g. the Aminolink aminoalylphosphoramidite linking agent (Applied Biosystems, Foster City, Calif.) and Biotin-X-NHS Ester available form Clontech Laboratodes (Palo Alto, Calif.).

A single 21-mer initializing oligonucleotide is employed with the following sequence:

(SEQ. ID:8) 5'-OP(=O)(O$^-$)O-CCTCTCCCTrCCCTCTCCTCC-3'

6-mer oligonucleotide probes are employed that have an acid labile phosphoramidate linkage between the 3'-most nucleoside and 3'-penultimate nucleoside of the probe, as shown in the following formula:

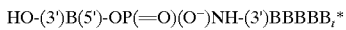

where $B_t^*$ is a JOE-, FAM-, TAMRA-, or ROX-labeled dideoxynucleoside, such that the label corresponds to the identity of the 3'-most nucleotide (so 16 different labeled dideoxynucleosides are used in the synthesis of the probes).

As above, the 6-mer probes are prepared in 96 stringency classes of 42 or 43 probes each (2 subsets for each of 48 different annealing temperatures). Hybridizations and ligations are carried out as described above. After ligation and washing, a nucleoside in the target polynucleotide is identified by the fluorescent signal of the oligonucleotide probe. Acid cleavage is then carried out by treating the extended duplex with 0.8% trifluoroacetic acid in dichloromethane for 40 minutes at room temperature to regenerate an extendable end on the extended duplex. The process continues until the sequence of the target polynucleotide is determined.

I claim:

1. A method for identifying a sequence of nucleotides in a polynucleotide, the method comprising the steps of:
   (a) extending an initializing oligonucleotide along the polynucleotide by ligating an oligonucleotide probe thereto to form an extended duplex;
   (b) identifying one or more nucleotides of the polynucleotide; and
   (c) repeating steps (a) and (b) until the sequence of nucleotides is determined.

2. A kit for DNA sequence analysis, the kit comprising one or more sets of oligonucleotide probes, wherein
   (i) each probe set contains at least 50 different-sequence, single-stranded oligonucleotide probes,
   (ii) the oligonucleotide probes of a set have a selected length of up to 12 nucleotides, and
   (iii) for at least one said probe set, the different-sequence, single stranded oligonucleotide probes in that set have annealing temperatures whose maximum and minimum values differ from each other by no more than 1° C.

3. The kit of claim 2, wherein each probe set contains from 50 to 10,000 different different-sequence, single-stranded oligonucleotide probes.

4. The kit of claim 2 wherein said annealing temperatures have a value from 22° C. to 70° C.

5. The kit of claim 4 wherein the oligonucleotide probes have lengths of 8, 9, or 12 nucleotides.

6. The kit of claim 2 which further includes an initializing oligonucleotide having a length of from 20 to 30 nucleotides, for binding to a target nucleic acid.

7. The kit of claim 3 further including one or more initializing oligonucleotides and one or more solid phase supports having templates attached thereto, the templates each comprising a target polynucleotide having a binding region capable of forming a perfectly matched duplex with one or more of the initializing oligonucleotides.

8. The kit of claim 3 wherein each probe set contains 50 to 500 different-sequence, single-stranded oligonucleotide probes.

* * * * *

US006306597C1

(12) EX PARTE REEXAMINATION CERTIFICATE (7394th)
United States Patent
Macevicz

(10) Number: US 6,306,597 C1
(45) Certificate Issued: *Mar. 2, 2010

(54) DNA SEQUENCING BY PARALLEL OLIGONUCLEOTIDE EXTENSIONS

(75) Inventor: Stephen C. Macevicz, 25861 Industrial Blvd., Hayward, CA (US) 94545

(73) Assignees: Illumina, Inc., Hayward, CA (US); Solexa, Inc., Hayward, CA (US); Stephen C. Macevicz, Hayward, CA (US)

Reexamination Request:
No. 90/009,205, Jun. 30, 2008

Reexamination Certificate for:
Patent No.: 6,306,597
Issued: Oct. 23, 2001
Appl. No.: 09/280,270
Filed: Mar. 29, 1999

( * ) Notice: This patent is subject to a terminal disclaimer.

Related U.S. Application Data

(60) Continuation of application No. 08/872,446, filed on Jun. 10, 1997, now Pat. No. 5,969,119, which is a division of application No. 08/424,663, filed on Apr. 17, 1995, now Pat. No. 5,750,341.

(51) Int. Cl.
| | |
|---|---|
| C12Q 1/68 | (2006.01) |
| G01N 33/00 | (2006.01) |
| C07H 21/02 | (2006.01) |
| C07H 21/04 | (2006.01) |

(52) U.S. Cl. .................... 435/6; 435/91.1; 435/91.2; 436/94; 536/23.1; 536/24.3; 536/24.33

(58) Field of Classification Search .................... None
See application file for complete search history.

(56) References Cited

U.S. PATENT DOCUMENTS

| | | | |
|---|---|---|---|
| 4,811,218 A | 3/1989 | Hunkapiller et al. ........ 204/461 |
| 4,883,750 A | 11/1989 | Whiteley et al. | |
| 4,988,617 A | 1/1991 | Landegren et al. | |
| 5,403,708 A | 4/1995 | Brennan et al. | |
| 5,407,798 A | 4/1995 | Martinelli et al. .............. 435/6 |
| 5,503,980 A | 4/1996 | Cantor .......................... 435/6 |
| 5,552,278 A | 9/1996 | Brenner ......................... 435/6 |
| 5,700,637 A | 12/1997 | Southern ....................... 435/6 |
| 5,798,210 A | 8/1998 | Canard et al. ................... 435/6 |
| 5,800,994 A | 9/1998 | Martinelli et al. | |
| 5,876,924 A | 3/1999 | Zhang et al. .................. 435/5 |
| 5,877,280 A | 3/1999 | Wetmur ...................... 530/350 |
| 5,972,619 A | 10/1999 | Drmanac et al. ................ 435/6 |
| 6,007,987 A | 12/1999 | Cantor et al. ................... 435/6 |
| 6,027,889 A | 2/2000 | Barany et al. .................. 435/6 |
| 7,070,927 B2 | 7/2006 | Drmanac | |

FOREIGN PATENT DOCUMENTS

| | | |
|---|---|---|
| EP | 0 372 524 A2 | 6/1990 |
| EP | 0 514 927 A1 | 11/1992 |
| GB | 2 236 852 B | 4/1991 |
| WO | WO 8912695 A1 | 12/1989 |
| WO | WO 91/06678 | 5/1991 |
| WO | WO 9317126 A1 | 9/1993 |
| WO | WO 94/11530 | 5/1994 |
| WO | WO 94/23064 | 10/1994 |
| WO | WO-95/04160 | 2/1995 |
| WO | WO-95/09248 | 4/1995 |
| WO | WO 95/09248 | 4/1995 |
| WO | WO 9535390 A1 | 12/1995 |
| WO | WO 9615271 A1 | 5/1996 |

OTHER PUBLICATIONS

Abravaya et al., "Detection of point mutations with a modified ligase chain reaction (Gap–LCR)," *Nucleic Acids Research*, vol. 23, No. 4, p. 675–682 (1995).

Abravaya et al., "Detection of Point Mutations with Ligase Chain Reaction" ASM General Meeting of the American Society for Microbiology (Las Vegas, NV) 1994.

Abravaya et al., "Detection of Single Base Changes with GAP–LCR: Factors that Affect Discrimination," *Clin. Chem.*, vol. 40, No. 4 (1994).

Akane et al., "Direct Dideoxy Sequencing of Genomic DNA by Ligation–Mediated PCR," *BioTechniques*, vol. 16, No. 2, Jan. 1994.

Barany, "Genetic Disease Detection and DNA Amplification Using Cloned Thermostable Ligase," *Proc. Natl. Acad. Sci. USA*, vol. 88, p. 189–193, Jan. 1991.

Barany, "The Ligase Chain Reaction in a PCR World," *PCR Methods and Applications*, vol. 1, No. 1, p. 5–16, Aug. 1991.

Cahill et al., "Polymerase Chain Reaction and Qβ Replicase Amplification," *Clin. Chem.*, vol. 37, No. 9, p. 1482–1485 (1991).

Cantor et al., "Report on the Sequencing by Hybridization Workshop," *Genomics*, vol.13, p. 1379–1383 (1992).

Cao, "Recent Developments in Ligase–Mediated Amplification and Detection," *TRENDS in Biotechnology*, vol. 22, No. 1, p. 38–44, Jan. 2004.

Carrino and Laffler, "Detection of HIV DNA Sequences Using the Ligase Chain Reaction (LCR)," *Clin. Chem.*, vol. 37, No. 6 (1991).

Carrino and Lee, "Nucleic acid amplification methods," *J. Microbiological Methods*, vol. 23, p. 3–20 (1995).

Chelly et al., "Transcription of the Dystrophin Gene in Human Muscle and Non–Muscle Tissues," *Nature*, vol. 333, No. 6167, p. 858–860, Jun. 30, 1988.

Day et al., "Detection of Steriod 21–Hydroxylase Alleles Using Gene–Specific PCR and a Multiplexed Ligation Detection Reaction," *Genomics*, vol. 29, p. 152–162 (1995).

Drmanac et al., "SBH and the Integration of Complementary Approaches in the Mapping, Sequencing, and Understanding of Complex Genomes," Technical Paper Presented at the International Conference on Bioinformatics, Supercomputing, and Complex Genome Analysis, St. Petersburg, FL (United States), Jun. 4–7, 1992.

(Continued)

*Primary Examiner*—Bruce Campell

(57) ABSTRACT

The present invention includes, in one aspect, a kit comprising one or more sets of oligonucleotide probes whose perfectly matched duplexes with complementary sequences have similar or substantially the same free energy of duplex formation.

OTHER PUBLICATIONS

Fainsod et al., "The homeo domain of a murine protein binds 5' to its own homeo box," *Proc. Natl. Acad. Sci. USA*, vol. 83, p. 9532–9536, Dec. 1986.

File History for U.S. Patent No. 6,855,523.

File History for U.S. Appl. No. 08/263,937.

File History for U.S. Appl. No. 08/344,203.

Gerry et al., "Universal DNA Microarray Method for Multiplex Detection of Low Abundance Point Mutations," *J. Mol. Biol.*, vol. 292, No. 2, p. 251–262 (1999).

Gilliland et al., "Analysis of cytokine mRNA and DNA: Detection and quantitation by competitive polymerase chain reaction," *Proc. Natl. Aca. Sci. USA*, vol. 87, p. 2725–2729, Apr. 1990.

Hsuih et al., "Novel, Ligation–Dependent PCR Assay for Detection of Hepatitis C Virus is Serum," *J. of Clin. Microbiology*, vol. 34, No. 3, p–501–507, Mar. 1996.

John K. Elder, "Image Processing in Nucleic Acid Sequence Analysis," Thesis submitted for the degree of Doctor of Philosophy, Dept. of Biochemistry and Trinity College, University of Oxford (1993).

Khrapko et al., "A Method for DNA Sequencing by Hybridization with Oligonucleotide Matrix," *DNA Sequence—DNA Sequencing and Mapping*, vol. 1, p. 375–388 (1991).

Khrapko et al., "Hybridization of DNA with Oligonucleotides Immobilized in Gel: Convenient Method for Recording Individual Base Changes," *Molekulyarnaya Biologiya*, vol. 25, No. 3, p. 718–730 (1991).

Kinzler and Vogelstein, "Whole genome PCR: application to the identification of sequences bound by gene regulatory proteins," *Nucleic Acids Research*, vol 17, No. 10, p. 3645–3653 (1989).

Kramer and Lizardi, "Replicatable RNA reporters," *Nature*, vol. 339, p. 401–402, Jun. 1, 1989.

Lafller et al., "The ligase chain reaction in DNA–based diagnosis," *Ann. Biol. Clin.*, vol. 50, p. 821–826 (1993).

Landegren et al., "A Ligase–Mediated Gene Detection Technique," *Science*, vol. 241, No. 4862, p. 1077–1080, Aug. 26, 1988.

Lizardi and Kramer, "Exponential amplification of nucleic acids: new diagnostics using DNA polymerases and RNA replicases," *TIBTECH*, vol. 9, p. 53–58, Feb. 1991.

Luo et al., "Improving the fidelity of *Thermus thermophilus* DNA ligase," *Nucleic Acids Research*, vol. 24, No. 14, p. 3071–3078 (1996).

Lysov et al., "A New Method for Determining the DNA Nucleotide Sequence by Hybridization with Oligonucleotides," Translated from Doklady Akademii Nauk SSR, vol. 303, No. 6, pp. 1508–1511, Dec. 1988.

Maskos and Southern, "A study of oligonucleotide reassociation using large arrays of oligonucleotides synthesized on a glass support," *Nucleic Acids Research*, vol. 21, No. 20, p. 4663–4669 (1993).

McNamara et al., "Development of a Multiplex PCR–Ligase Detection Reaction Assay for Diagnosis of Infection by the Four Parasite Species Causing Malaria in Humans," *J. Clinical Microbiology*, p. 2403–2410, Jun. 2004.

Mirzabekov, "DNA Sequencing by Hybridization—a Megasequencing Method and a Diagnostic Tool?" *TIBTECH*, vol. 12, p. 27–32, Jan. 1994.

Nickerson et al., "Automated DNA diagnostics using an ELISA–based oligonucleotide ligation assay," *Proc. Natl. Acad. Sci. USA*, vol. 87, p. 8923–8927, Nov. 1990.

Nilsson et al., "Padlock Probes: Circularizing Oligonucleotides for Localized DNA Detection," *Science*, vol. 265, p. 2085–2088, Sep. 30, 1994.

Park, et al., "Detection of Hepatitis C Virus RNA Using Ligation–Dependent Polymerase Chain Reaction in Formalin–Fixed, Paraffin–Embedded Liver Tissues," *Am. J. of Pathology*, vol 149, No. 5, p. 1485–1491, Nov. 1996.

Pfeifer et al., "Genomic Sequencing and Methylation Analysis by Ligation Mediated PCR," *Science*, vol 246, p. 810–813, Oct. 6, 1989.

Punwaney et al., "Human Papillomavirus may be Common within Nasopharyngeal Carcinoma of Caucasian American: Investigation of Epstein–Barr Virus and Human Papillomarvirus in Easterns and Western Nasopharyngeal Carcinoma Using Ligation–Dependent Polymerase Chain Reaction," *Head & Neck*, vol. 21, No. 1, p. 21–29, Jan. 1999.

Smith, "Ligation–mediated PCR of Restriction Fragments from Large DNA Molecules," *PCR Methods and Applications*, Aug. 1992, vol. 2, No. 1, p. 21–27.

Southern et al., "Analyzing and Comparing Nucleic Acid Sequences by Hybridization to Arrays of Oligonucleotides: Evaluation Using Experimental Models," *Genomics*, vol. 13, p. 1008–1017 (1992).

Strezoska et al., "DNA sequencing by hybridization: 100 bases read by a non–gel–based method," *Proc. Natl. Acad. Sci. USA*, vol. 88, p. 10089–10093, Nov. 1991.

U.S. Department of Energy, Office of Energy Research Grant Proposal, "Sequencing of DNA by Hybridization with oligonucleotides matrix (SHOM)," Mirzabekov (Principal Investigator), Mar. 30, 1992.

Mag et al., "Synthesis and Selective Cleavage of an Oligodeoxynucleotide Containing a Bridged Non–Chiral Internucleotide 3'–Phosphoramidate Linkage", Tetrahedron Letters 33(48):7319–7322 (1992).

Wang et al., "Molecular Genetic and Genetic Correlations in Sodium Channelopathies: Lack of Founder Effect and Evidence for a Second Gene," *Am. J. Hum. Genet.*, vol. 52, p. 1074–1084 (1993).

Wiedmann et al. "Detection of *Listeria monocytogenes* with a Nonisotopic Polymerase Chain Reaction–Coupled Ligase Chain Reaction Assay," *Applied and Environmental Microbiology*, vol. 59, No. 8, p. 2743–2745, Aug. 1993.

Wiedmann et al., "Discrimination of Other *Listeria* Species by Ligase Chain Reaction," *Applied and Environmental Microbiology*, vol. 58, No. 11, p. 3443–3447, Nov. 1992.

Wiedmann et al., "Ligase Chain Reaction (LCR)—Overview and Applications," *PCR Methods and Applications*, vol. 3, No. 4, p. S51–S64, Feb. 1994.

Wilson et al., "Frequency of oncogenic point mutations in human tissues determined by combined PCR and LCR techniques," *Proceedings of the American Association for Cancer Research*, vol. 34, p. 262, Mar. 1993.

Wu and Wallace, "The Ligation Amplification Reaction (LAR)—Amplification of Specific DNA Sequences Using Sequential Rounds of Template–Dependent Ligation," *Genomics*, vol. 4, p. 560–569 (1989).

Yarkin et al., "Detection of HPV DNA in Cervical Specimens Collected in Cytologic Solution by Ligation–Dependent PCR," *J. of Clin. Cytology and Cytopathology*, May–vol. 7, No. 3, p. 450–456, Jun. 2003.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claim 1 is confirmed.

New claims 9–13, 15–20 and 24 are added and determined to be patentable.

Claims 2–8 were not reexamined.

9. *The method of claim 1, wherein the polynucleotide comprises a binding region and a target polynucleotide.*

10. *The method of claim 9, wherein the binding region comprises a known sequence and the target polynucleotide comprises an unknown sequence; and wherein in step (a) the initializing oligonucleotide is hybridized to the binding region on the polynucleotide.*

11. *The method of claim 1, wherein the oligonucleotide probe of step (a) comprises a chemically scissile internucleosidic linkage.*

12. *The method of claim 11, wherein after step (b), the method further comprises*

*(d) treating the polynucleotide with a chemical agent to cleave the chemically scissile internucleosidic linkage; and*

*wherein step (c) further comprises repeating step (d).*

13. *The method of claim 11, wherein after step (b), the method further comprises*

*(d) treating the polynucleotide with light to cleave the chemically scissile internucleosidic linkage; and*

*wherein step (c) further comprises repeating step (d).*

14. *The method of claim 1, wherein the oligonucleotide probe comprises a label which results in a spectrally resolvable fluorescent signal.*

15. *The method of claim 14, wherein the identity of the one or more nucleotides of the polynucleotide is correlated to a distinct color of the spectrally resolvable fluorescent signal.*

16. *The method of claim 1, wherein the oligonucleotide probe comprises one or more deoxyinosine bases.*

17. *The method of claim 1, wherein before step (a), the method further comprises*

*(d) providing a plurality of different oligonucleotide probes to the polynucleotide.*

18. *The method of claim 17, wherein each probe in the plurality of different oligonucleotide probes comprises a label, and wherein the label represents a base.*

19. *The method of claim 17, wherein each probe in the plurality of different oligonucleotide probes has a predetermined length selected from the group consisting of 8 nucleotides, 9 nucleotides, and 12 nucleotides.*

20. *The method of claim 1, wherein the polynucleotide is attached to a solid phase support, and wherein the solid phase support comprises a bead.*

\* \* \* \* \*